United States Patent [19]

Washburn et al.

[11] 4,061,565

[45] Dec. 6, 1977

[54] SORPTION OF WEAK ORGANIC ACIDS FROM WATER BY POLYURETHANE

[75] Inventors: Owen Victor Washburn, Fredericton; Georgeos Konstandenos Kouvarellis; William Alexander Ferguson, both of Guelph, all of Canada

[73] Assignee: Uniroyal, Ltd., Canada

[21] Appl. No.: 613,846

[22] Filed: Sept. 16, 1975

[30] Foreign Application Priority Data

July 8, 1975 Canada .................................. 231051

[51] Int. Cl.² ............................................ B01D 15/06
[52] U.S. Cl. ...................................... 210/32; 210/40
[58] Field of Search ............... 208/263; 210/24, 30 A, 210/40, DIG. 26, 30 R, 32; 260/29.2 TN, 75 TN, 77.5 AP

[56] References Cited

U.S. PATENT DOCUMENTS

| | | | |
|---|---|---|---|
| 3,597,351 | 8/1971 | Landenburg et al. | 210/32 |
| 3,617,531 | 11/1971 | Schlicht et al. | 208/263 |
| 3,812,031 | 5/1974 | Mc Coy et al. | 210/40 |
| 3,883,465 | 5/1975 | Olstowski | 260/77.5 AP |
| 3,905,925 | 9/1975 | Vervloet | 260/77.5 AP |

*Primary Examiner*—Wilbur L. Bascomb, Jr.
*Assistant Examiner*—Ivars Cintins
*Attorney, Agent, or Firm*—Anthony Lagani, Jr.

[57] ABSTRACT

The separation and recovery of weakly acidic organic substances from aqueous solution by means of granules of unblown polyurethane.

27 Claims, No Drawings

SORPTION OF WEAK ORGANIC ACIDS FROM WATER BY POLYURETHANE

This invention is concerned with the separation of weakly acidic, monomeric organic substances from aqueous solutions by means of granules of porous and-/or non-porous unblown polyurethane, and recovery of the acidic substances from the granules.

The substances to be recovered include phenols and phenolic substances, and weak carboxylic acids. Such materials are often encountered in the outflow from various industrial processes, and must be removed from the water, either because of their intrinsic value or because, if left in the water, they would be regarded as pollutants of the environment.

Polyurethanes are well-known and widely used commercial materials prepared in known manner by interaction of aromatic polyisocyanates and a wide variety of polyether glycolic materials.

PRIOR ART

H. J. M. Bowen, in J. Chem. Soc. (A) (1970), pages 1082-85, shows the absorption of phenol from water by polyurethane foam whose bulk density was in the range between 15 and 35 kg/m$^3$, — that is, between 0.015 and 0.035 g/cm$^3$. The reported absorption capacity was equal to or somewhat greater than 0.032 mole of phenol per kilogram of foam, — that is, at least 3.0 milligrams of phenol were absorbed per gram of foam.

McCoy et al., in U.S. Pat. No. 3,812,031 (1970), show the separation of phenolic materials from water solution by adsorption upon polyurethane foam containing hydrophilic fibers, followed by elution with acetone or hot water. For such use the polyurethane foam is ground or shredded to a size of about 10-mesh (so as to pass through a screen having ten openings per lineal inch). From the weight of polyurethane foam used by McCoy et al. to fill a column of given dimensions, it is readily calculated that their foam had a bulk density between 0.04 and 0.05 g/cm$^3$. The use of such foam requires a column or other vessel of comparatively large volume relative to the weight of polyurethane employed.

Since the weight of phenol taken up depends, other factors being constant, upon the weight of polyurethane used, it is clear that the space requirements in these prior methods are high, particularly for installations of large capacity. The space requirements of the prior methods are found to be from ten to twenty times those of our method, for the same absorption capacity.

The sorption of phenols by anion exchange resins is discussed by M. G. Chasanov et al. in Ind. & Eng. Chem., vol. 48 (1956), pp. 305-309.

The sorption of phenolics from aqueous media by insoluble basic polymers and copolymers containing nitrogenous basic or cationic groups, typified by the dialkylaminoalkylimide derivatives of olefin/maleic acid or anhydride copolymers, is disclosed by K. Landenburg et al. in U.S. Pat. No. 3,597,351. Control of the pH is suggested, in a manner not explained, but said to be based on the nature of the sorbent and material being sorbed; and the pH is to be such that the sorbent is protonated and bears a positive charge. It is stated that lowering the pH may cause suspended colloidal matter to lose its usual negative charge, so that sorption is somewhat impaired. Specific pH values are discussed only with reference to the clarification of beer having a pH of about 3 to 6, usually 4 to 5, and naturally containing tannins. The basic polymers are said to be efficient in removing phenolics from water at pH 3 to 9, no guide being given as to the relation between pH and any property of the phenolic being sorbed, nor any rule by which to select the optimum pH.

THE INVENTION

The process of our invention utilizes unblown granular polyurethanes, which may be porous or non-porous, for absorbing phenolics and weak carboxylic acids from aqueous solutions under carefully controlled pH conditions, whereby we use the absorption capacity of the polyurethanes to the fullest possible extent. The space requiements for the equipment are minimal. The particle size of the polyurethane granules is selected so as to achieve as high a rate of absorption as possible for any given application. The process also provides for recovery of the absorbed material from the absorbent under specified pH conditions.

We have discovered that maximum absorption of phenols and weak carboxylic acids from water solution by polyurethane resin occurs when the hydrogen ion concentration of the water is such that its pH value is lower, preferably by at least two units, than the pK$_a$ value of the material to be absorbed. (The pK$_a$ of an acid is defined as -log$_{10}$ of its acid dissociation constant.) If the pH is raised above the indicated value, the absorption capacity of the polyurethane falls off rapidly. Indeed, absorption of phenols and weak acids from water having a pH equal numerically to the pK$_a$ of the phenol or acid is reduced by about 50 percent, and approaches zero as the pH approaches a value two units higher than said pK$_a$ value.

Describing these relationships more particularly, we have found that, when we plot the theoretical curve for a given weak acid or phenol in water solution in terms of fraction undissociated versus pH, and plot the equilibrium absorption capacity of the polyurethane for that acid or phenol against pH, the two curves have essentially the same form and follow similar courses. The absorption capacity begins to fall off at the pH at which the acid or phenol begins to dissociate. The absorption capacity thereafter decreases rapidly, corresponding to the increase in the degree of dissociation of the dissolved absorbate, and reaches a steady minimum value at or close to zero at the pH at which the absorbate becomes virtually fully dissociated. Hence, with knowledge of the pk$_a$ of a given weak acid or phenol, one can predict the pH range in which the equilibrium absorption will be maximum. We have verified this phenomenon over a wide pH range.

We have further found that complete separation of the absorbate from the polyurethane is achieved by contacting the absorbate-laden granules with water having a pH at least two units higher than the pK$_a$ of the absorbate. Thus, for phenol, of pK$_a$ 9.8, maximum absorption occurs at any pH below and up to 7.8. As the pH rises above 7.8, the absorption capacity decreases rapidly, approaching zero at pH 11.8. Similarly, maximum absorption of 2,4-dichlorophenol, of pK$_a$ 7.6, occurs at any pH below and up to 5.6. With increasing pH, the equilibrium absorption capacity decreases rapidly, approaching zero at pH 9.6 and above.

From the above considerations it follows that selective absorption from aqueous solutions of weakly acidic substances of differing pK$_a$ values should also be possible. Thus, if two substances differing in pK$_a$ value by at least four units are dissolved in water, the one of higher $pK_a$ value should be absorbed to the exclusion of the other, if the pH of the solution is controlled in accordance with the principles set forth above. Thus, from water containing two weakly acidic substances differing in $pK_a$ by at least four units, the weaker one, having the higher $pK_a$, will be absorbed exclusively if the pH is midway between the two $pK_a$ values.

The behavior described derives from the variation in degree of dissociation of weak acids with change in pH of the aqueous medium, and from the fact that polyurethanes absorb only the undissociated molecules of the weak acids and phenols, and do not significantly absorb the corresponding dissociated anions. The process, then, is essentially non-ionic in character. The high solubility of phenols and weak acids in polyurethanes is believed to be due to hydrogen bonding of the undissociated molecules to oxygen and/or nitrogen atoms of the polyurethane chains. At saturaton there is a close one-to-one correlation between the number of chemical equivalents of bonding sites and the number of equivalents of a phenol or acid absorbed.

Since both water and polyurethane are solvents for phenols and weak organic acids, there is a competition in our process between the two solvents for the solute-absorbate molecules. Thus, our absorption process depends on the very high solubility of the absorbate molecules in polyurethane relative to their solubility in water, the distribution being heavily weighted in favor of the polyurethane. In the desorption step, on the other hand, the distribution is in favor of the aqueous alkaline phase, in which the absorbate molecules are highly ionized and hence very soluble, whereas the absorbate ions are only slightly soluble in polyurethane.

Accordingly, the invention comprises the step of contacting an aqueous solution of weakly acidic material with granules of porous and/or non-porous unblown polyurethane until substantial sorption of acidic materials has occurred, the solution having a pH lower, preferably by at least two units, than the $pK_a$ value of the acidic substance to be absorbed. The acidic material is then eluted from the polyurethane in situ, preferably by means of water having a pH at least two units higher than the $pK_a$ value of the absorbate. The eluted material may then be recovered by any desired conventional means.

The regenerated polyurethane may be used repeatedly, remaining unchanged through many cycles of absorption and regeneration.

Our process is carried out by placing a quantity of unblown polyurethane granules in a bed or a column and contacting the contaminated water with the granules. Either a batch method or a continuous method may be used. The contaminated water is shaken with the absorbent, or is passed through one or more beds or columns of absorbent in serial fashion, spent columns being replaced by fresh ones in known manners. The absorbed acidic material is then recovered from the absorbent by elution with a suitable polar solvent, e.g., acetone, or with a water solution having a pH higher than the $pK_a$ value of the absorbed acid, as disclosed herein.

The range of $pK_a$ values for the acidic materials to which our invention is applicable is from about 3.0 to about 11.0. The weak carboxylic acids have $pK_a$ values of from 3 to 6, and the phenols have $pK_a$ values from 4 to 11. Examples of such acids include crotonic acid, benzoic acid, 3-nitrobenzoic acid, cinnamic acid, 2,4-dichlorophenoxyacetic acid, 2,4,5-trichlorophenoxyacetic acid. Examples of such phenols are the monocyclic monophenols including phenol, o-cresol, m-cresol, p-cresol, cresylic acid, chlorophenols, 2,4-dichlorophenol, nitrophenols such as p-nitrophenol and 2,4-dinitrophenol, 2,4-dimethylphenol, 2,6-dimethylphenol, and 2,4,6-trimethylphenol; polycyclic phenols including alpha-naphthol, beta-naphthol; and polyhydric phenols including catechol, resorcinol, and hydroquinone.

The $pK_a$ values of some of these acids and phenols are shown in the following table:

| Weak Acid | $pK_a$ Value |
|---|---|
| crotonic | 4.7 |
| t-cinnamic | 4.4 |
| 2,4-dichlorophenoxyacetic | 3.31 |
| o-cresol | 10.20 |
| m-cresol | 10.0 |
| p-cresol | 10.17 |
| cresylic* | 10.0–10.20 |
| 2-chlorophenol | 8.48 |
| 3-chlorophenol | 9.02 |
| 4-chlorophenol | 9.38 |
| 2,4-dimethylphenol | 10.49 |
| 2,4-dinitrophenol | 4.09 |
| B-naphthol | 9.93 |

*Cresylic acid, some mixture of o-, m- and p- cresols, likely has an average $pK_a$ value in the range 10.0–10.20.

By using granules of porous and/or non-porous, unblown polyurethane in our process, we are able to use small, compact equipment, occupying on the order of only one-twentieth to one-fifth of the space required for equipment of the same absorption capacity using polyurethane foam. Cost savings are apparent.

The rates of absorption attainable with our solid granules ae comparable with those attained with foam.

In our process, the absorption rates are dependent on the granule size and on the temperature. The rate of absorption by a given weight of polyurethane increases very markedly with decreasing granule size. The rate of absorption also increases with rising temperature, although, as will be shown, the equilibrium absorption capacity decreases with rising temperature in the range between 0° and 100° C. Hence, in practice, a temperature at which to operate the process will be selected which provides both an absorption rate and an absorption capacity that are acceptable in a given situation. Below the acceptable temperature range the absorption capacity would be higher and the absorption rate lower, whereas above the acceptable temperature range, the absorption rate would be higher and the capacity lower. For most purposes we have found the optimum temperature range to be from about 10° to about 45° C.

To illustrate further the relation of temperature to the equilibrium absorption capacity in our system, we determined the absorption capacity of a polyurethane at various temperatures for several equilibrium concentrations of 2,4-dichlorophenol in water. For an equilibrium concentration of 748 milligrams of the chlorophenol per liter of solution, the equilibrium absorption capacity was 194 milligrams of the chlorophenol per gram of polyurethane at 87° C, 495 mg/g at 45° C, and 620 mg/g at 25° C. For an equilibrium concentration of 422 mg/l, the equilibrium absorption capacity was 260 mg/g at 51° C., 340 mg/g at 45° C., and 460 mg/g at 25° C. For an equilibrium concentration of 185 mg/l, the equilibrium absorption capacity was 190 mg/g at 45° C., 290 mg/g at 25° C., and 415 mg/g at 0° C. The equilibrium capacity is seen to be an inverse straight-line function of temperature over the range between 0° and 100° C.

The following data illustrate the relation of granule size to the time required to reach maximum absorption, using 2,4-dichlorophenol at a temperature of 25° C, a pH of 4.0 and at an initial concentration of 1930 milligrams per liter. The absorbent was an unblown polyurethane prepared by the interaction in acetone, at room temperature, of an 80:20 mixture of 2,4- and 2,6-toluene diisocyanates with a polyol derived from glycerol, propylene oxide and ethylene oxide.

| Mesh Size | Equilibrium Absorption Time |
| --- | --- |
| 4—6 | 21 hours |
| 8—12 | 10 hours |
| 18—25 | 6 hours |
| 42—100 | 1 hour |
| 100—400 | 5 minutes |

Since in a batch process there are no problems of liquid flow, the most rapid absorption is obtained by using polyurethane granules of as small a size as possible. The range from 400-mesh to 100-mesh is optimum. However, in a column or tower operation, since the pressure drop through the column increases with decreasing particle size, the use of very fine particles of absorbent becomes impractical. We have found the optimum particle sizes for column operation to be in the range from about 25-mesh to about 12-mesh. With sizes larger than 12-mesh, the absorption rate may become impracticably low for most uses.

Various preparations of polyurethane have a maximum absorption capacity for phenols and weak acids equal to from 500 to 3000 milligrams of absorbate per gram of absorbent. In using our process it is, of course, not necessary that the maximum possible absorption be achieved; it is usually more efficient and economical to allow absorption to proceed so long as the effluent concentration remains at a low, virtually constant value, or the absorption rate remains above a fairly constant selected value. A column operation will be continued until the effluent concentration is no longer virtually constant but begins to rise rapidly. At such break point, the absorption may be terminated in the first column and the flow directed to a second, fresh column.

For example: in a typical run, 200 grams of a polyurethane (described above) is placed in a column through which is flowed, at 10 ml/min, an aqueous solution of 2,4-dichlorophenol having an initial concentration of 1000 milligrams per liter and a pH of 4, at a temperature of about 25° C. The effluent concentration remains steady at 2 to 5 milligrams per liter for 150 hours, then starts to rise rapidly, signifying that the absorbent is approaching saturation. At this point, the inflow is directed to another column, and the first column is subjected to the regeneration process which both recovers the absorbate and returns the absorbent to its original condition, ready for another absorption cycle.

In a comparable run, under the same conditions of concentration, flow rate, and temperature, but substituting activated carbon for polyurethane, the effluent concentration reached the break point in only 70 hours.

Our process, as described for absorption of 2,4-dichlorophenol, also works effectively for all of the phenolics and weak acids listed above and is likewise applicable to all such compounds having $pK_a$ values within the specified range.

The regeneration step is accomplished, as indicated above, by contacting the absorbate-laden granules with water having a pH preferably two or more units higher than the $pK_a$ of the absorbate. In a batch process, they are immersed in a quantity of the leaching solution for a time sufficient for complete dissolution of the absorbate from the granules. In a column operation, the eluting solution is passed through the bed of granules in which the absorption has taken place. The eluting solution is usually dilute sodium hydroxide or calcium hydroxide. To ensure complete removal of the absorbate, we find it desirable to use a number of equivalents of the alkali which is from 10% to 100% in excess of the number of equivalents of absorbate to be eluted. The elution may also be done with a polar solvent such as acetone, methanol, or isopropanol, if it is so desired.

As an example, 0.5 gram of polyurethane granules which had absorbed 776.5 mg of 2,4-dichlorophenol by our method was left in contact with 30 ml. of 0.1N sodium hydroxide solution for 24 hours at 25° C. Desorption of the chlorophenol from the polyurethane was found to be 100%. Similar results are obtained when the absorbate is any phenol or weak acid such as those previously listed.

We have observed that when a phenol is absorbed by polyurethane granules, the granules swell, the degree of swelling being directly proportional to the amount of absorbate taken up. The potential expansion is to be taken into account in the designing of equipment for use in our process.

Preparation of polyurethanes. Typical polyols used commercially in the manufacture of polyurethanes include the following:

a. products of the reaction of propylene oxide and ethylene oxide with glycerol: functionality, 3;

b. "polybutadienediol"—that is, poly (2-butene-1,4-ylene)diol: functionality, 2;

c. products of the reaction of propylene oxide with sucrose and sorbitol: average functionality, 7;

d. poly(1,4-butanediol): functionality, 2;

e. poly(ethylene glycol adipate): functionality, 2;

f. poly(ethylene glycol): functionality, 2;

g. diethylene glycol: functionality, 2.

Many other diols and polyols of a character analogous to those are available, as is well known in the art.

Typical polyisocyanates used in the preparation of polyurethanes include:

a. 80:20 mixture of 2,4- and 2,6-toluene diisocyanates; and b. mixtures of p,p'-diphenylmethane diisocyanate and dibenzylbenzene triisocyanate, in various ratios to provide functionalities between 2.0 and 3.0.

An exemplary polyurethane having optimum absorption and physical properties for use in our invention is made by reacting the following mixture:

| | |
| --- | --- |
| glycerol/propylene oxide/ethylene oxide reaction product | 100 g. |
| toluene diisocyanate | 42.4 g. |
| acetone (anhydrous) | 400–600 ml. |
| water | 3.6 g. |
| Dabco 33LV (catalyst) (see Note 1) | 1.0 ml. |
| T-12 (catalyst) (see Note 2) | 0.5 ml. |

Note 1: Dabco 33LV is a 33% solution of triethylenediamine in propylene glycol.
Note 2: T12 is a dibutyltin dilaurate complex.

Heating the mixture for hour at its boiling point ensures completion of the reaction. The resulting suspension of swollen polyurethane is quite fluid. It is poured into a large excess of distilled water (say, 1.5–2.0 liters) to precipitate the polyurethane as granules ranging in size from 10-mesh to 100-mesh. The granules may, of course, be broken up and separated into lots of any desired ranges of size. The bulk of the material is in the 25- to 42-mesh range.

When the reaction is carried out, as here, in the absence of any surfactant, the $CO_2$ liberated does not generate foam but merely escapes into the atmosphere.

The granules thus prepared have the capability to rapidly absorb phenol from a 1% water solution of phenol, equilibrium being reached in two minutes.

Polyurethane granules, having intrinsically an absolute density of the order of 1.0, have a bulk density considerably lower than 1.0, because the irregular shapes and the loose packing of the granules create open spaces between the granules. Over the wide range of granule sizes useful in our process, the granules generally have a bulk denisty between 0.25 and 0.5 (that is, 0.25–0.5 g. occupies a volume of 1 cc.). This is in marked contrast to the very low densities of the polyurethane foams of the prior art, wherein McCoy et al. (loc. cit.) use foams estimated to have a density of 0.044 or somewhat greater, and Bowen (loc. cit.) reports foam densities of from 0.015 to 0.035 $g/cm^3$. It is seen that our unblown polyurethane granules have a bulk density on the order of five to twenty times that of the foams used by prior workers; correspondingly, the space requirements for absorption vessels in our process are one-twentieth to one-fifth of those for prior processes using foams.

We claim:

1. The method of extracting a weakly acidic, monomeric organic substance from an aqueous solution thereof which comprises contacting said solution, having a pH value less than the $pK_a$ value of said acidic substance, with granules of unblown polyurethane resin for a sufficient time to permit absorption of a substantial amount of said acidic substance from said solution by said resin granules.

2. The method of claim 1 wherein the granules have a bulk density of at least 0.25 gram per cubic centimeter.

3. The method of claim 1 wherein the granules are of a particle size of 12-mesh or smaller.

4. The method of claim 1 wherein the absorption is carried out at temperatures in the range 0° to 100° C.

5. The method of claim 1 wherein the absorption is carried out at temperatures in the range 10° to 45° C.

6. The method of claim 1 wherein the absorption is carried out while said solution is at a pH value at least 2 pH units less than the $pK_a$ value of the acidic substance.

7. The method of claim 1 wherein the acidic substance is phenolic.

8. The method of claim 1 wherein the acidic substance is a chlorinated phenol.

9. The method of claim 1 wherein the acidic substance is an alkylated phenol.

10. The method of claim 1 wherein the acidic substance is a cresol.

11. The method of claim 1 wherein the acidic substance is phenol.

12. The method of claim 1 wherein the acidic substance is a dihydric phenol.

13. The method of claim 1 wherein the acidic substance is a polycyclic phenol.

14. The method of claim 1 wherein the acidic substance is beta-naphthol.

15. The method of claim 1 wherein the acidic substance is a carboxylic acid.

16. The method of claim 1 wherein the acidic substance is a weak organic caboxylic acid.

17. The method of claim 1 wherein the acidic substance is an aryloxy-substituted alkanoic acid.

18. The method of claim 1 wherein the acidic substance is 2,4-dichlorophenoxyacetic acid.

19. The method of claim 1 wherein the acidic substance is an aromatic carboxylic acid.

20. The method of claim 1 wherein the acidic absorbate is recovered from the absorbent resin by contacting the resin containing the absorbate with water having a pH at least two units higher than the $pK_a$ value of the absorbate.

21. The method of claim 1 wherein the acidic absorbate is recovered from the absorbent resin by contacting the resin containing the absorbate with a polar organic solvent.

22. The method of claim 21 wherein the solvent is selected from methanol, acetone, and isopropanol.

23. The method of claim 1 wherein a fixed volume of aqueous solution containing weakly acidic material to be absorbed is contacted with a sufficient amount of the polyurethane resin granules to absorb at least a great part of the acidic material.

24. The method according to claim 23 wherein the particle size of the resin granules is in the range from 400-mesh to 100-mesh.

25. The method of claim 1 wherein the aqueous solution of the material to be absorbed is flowed through a quantity of the polyurethane resin at such a rate as to permit substantial absorption of the acidic material by the resin.

26. The method of claim 25 wherein the flow is maintained so long as the absorbate concentration in the effluent water remains essentially constant.

27. The method according to claim 25 wherein the particle size of the resin granules is in the range from 25-mesh to 12-mesh.

* * * * *